(12) United States Patent
Luy et al.

(10) Patent No.: US 8,889,382 B2
(45) Date of Patent: Nov. 18, 2014

(54) **PROCESS FOR CULTIVATING MICROORGANISMS OF THE GENUS *THRAUSTOCHYTRIALES***

(76) Inventors: Markus Luy, Neu-Anspach (DE); Matthias Rüsing, Köln (DE)

( * ) Notice: Subject to any disclaimer, the term of this patent is extended or adjusted under 35 U.S.C. 154(b) by 1049 days.

(21) Appl. No.: 10/578,965

(22) PCT Filed: Nov. 10, 2004

(86) PCT No.: PCT/EP2004/012715
§ 371 (c)(1),
(2), (4) Date: May 10, 2006

(87) PCT Pub. No.: WO2005/045050
PCT Pub. Date: May 19, 2005

(65) Prior Publication Data
US 2007/0141686 A1      Jun. 21, 2007

(30) Foreign Application Priority Data
Nov. 10, 2003    (DE) .................................. 103 52 837

(51) Int. Cl.
*C12P 7/64*          (2006.01)
*C12N 1/00*         (2006.01)
(52) U.S. Cl.
USPC .......................................... 435/134; 435/243
(58) Field of Classification Search
None
See application file for complete search history.

(56) References Cited

U.S. PATENT DOCUMENTS

| | | | | |
|---|---|---|---|---|
| 6,509,178 B1 * | 1/2003 | Tanaka et al. | .................. | 435/134 |
| 6,582,941 B1 * | 6/2003 | Yokochi et al. | ............... | 435/134 |

FOREIGN PATENT DOCUMENTS

| | | |
|---|---|---|
| EP | 0113183 A1 | 7/1984 |
| EP | 0823475 A1 | 2/1998 |
| JP | 01247079 | 10/1989 |
| JP | 08196288 | 8/1996 |
| WO | WO 91/11918 A1 | 8/1991 |
| WO | WO 96/33263 A1 | 10/1996 |
| WO | WO 98/03671 A1 | 1/1998 |

OTHER PUBLICATIONS

Artemis P. Simopoulos, "Essential fatty acids in health and chronic disease," Am.J.Clin.Nutr., American Society for Clinical Nutrition, No. 70, p. 560S-569S, (1999).
GISSI-Prevenzione Investigators, "Dietary supplementation with n-3 polyunsaturated fatty acids and vitamin E after myocardial infarction; results of the GISSI-Prevenzione trial," The Lancet, p. 447-455, (Aug. 7, 1999).
Author Unknown, "Medical Act (1858) Amendment Bill," The Lancet, p. 757-761, (Nov. 26, 1870).
Penny M. Kris-Etherton et al., "Fish Consumption, Fish Oil, Omega-3 Fatty Acids, and Cardiovascular Disease," Circulation, p. 2747-2757, (Nov. 19, 2002).
N. Gamez-Meza et al., "Seasonal Variation in the Fatty Acid Composition and Quality of Sardine Oil from Sardinops sagax caeruleus of the Gulf of California," Communication, AOCS Press, p. 639-642, (1999).
K. W. Fan et al., "Physiological Studies of Subtropical Mangrove *Thraustochytrids*," Botanica Marina, Walter de Gruyter (Berlin/New York), p. 50-57, (2002).
Zhi-You Wen et al., "Heterotrophic production of eicosapentaenoic acid by mircoalgae," Biotechnology Advances, 21 ed., Elsevier, p. 273-294, (Apr. 11, 2003).
P.K. Bajpai et al., "Optimization of Production of Docosahexaenoic Acid (DHA) by *Thraustochytrium aureum* ATCC 34304," Journal of the American Oil Chemists' Society, vol. 68( No. 7), p. 509-514, (Jul. 1991).
Iwao Iida, et al., "Improvement of Docosahexaenoic Acid Production in a Culture of *Thraustochytrium aureum* by Medium Optimization," Journal of Fermentation and Bioengineering 1996 ed., (vol. 81), (Issue. 1), (p. 76-78).

* cited by examiner

Primary Examiner — Vera Afremova

(57) ABSTRACT

The invention relates to an optimized method for the production of PUFAs by cultivating microorganisms belonging to the group of Stramenopiles in a fermentation medium that is pH-stabilized using calcium carbonate and comprises 3-15 g/L CaCO3, whereupon the PUFAs are isolated from the microorganisms and/or the medium. The invention particularly relates to novel optimized media having a different CaCO3 content. By using adequate quantities of CaCO3, the process can be significantly simplified during fermentation while greater quantities of DHA can be obtained at an increased oil content in the biomass. They allow microorganisms belonging to the Stramenopiles to be fermented without controlling the pH, thereby substantially improving and significantly simplifying PUFA production.

6 Claims, No Drawings

PROCESS FOR CULTIVATING MICROORGANISMS OF THE GENUS THRAUSTOCHYTRIALES

Different PUFAs (polyunsaturated fatty acids) and particularly omega-3 fatty acids (n-3 fatty acids) are essential components of the human nutrition.

It is, however, known that in the majority of industrialized nations, the supply of n-3 fatty acids is insufficient. In contrast to that, the overall proportion of fat in the diet, as well as the intake of saturated fatty acids and n-6 fatty acids, is too high. This is due to a change in the composition of our diet, which has occurred especially in the last approx. 150 years, and which is being linked (Simopoulos, A. P., 1999, Am. J. Clin. Nutr. 70, 560-569) to the appearance of different chronic diseases of civilization, such as, for example, cardiovascular diseases—the main cause of death in industrialized nations. A great number of studies has meanwhile shown that by means of a targeted increase in the intake of n-3 fatty acids, in particular of eicosapentaenoic acid (EPA) and docosahexaenoic acid (DHA), it is possible to significantly reduce the cardiovascular risk (GISSI-Prevenzione Investigators (Gruppo Italiano per lo Studio della Sopravvivenza nell'Infarto miocardico), 1999, Dietary supplementation with n-3 polyunsaturated fatty acids and vitamin E after myocardial infarction: results of the GISSI-pevenzione trial., Lancet 354, 447-455; Burr et al., 1989, Effects of changes in fat, fish, and fiber intake on death and myocardial reinfarction: diet and reinfarction trial (DART). Lancet 2, 757-761). Accordingly, many different organizations (WHO, FAO, AHA, ISSFAL, British Nutrition Foundation, etc.) recommend a significant increase in the intake of n-3 fatty acids (Kris-Eherton et al., Fish Consumption, Fish Oil, Omega-3 Fatty Acids, and Cardiovascular Disease. Circulation 2002, 2747-2757).

Sources of PUFAs and, in particular, n-3 fatty acids are especially marine coldwater fish and the oils extracted therefrom, but also marine microorganisms, which, compared to fish, have the advantage that they can be used for producing PUFAs under cost effective and controlled conditions. Fermentative production does not pose any contamination risk, as is often described for fish or the fish oils extracted therefrom (Olsen SF. Int J Epidemiol. 2001: 1279-80). In addition, the composition of the extracted oils can be can be positively influenced by selecting the organism and the culture conditions and is not subjected to seasonal variations, as described for fish and fish products as well (Gamez-Meza et al. Lipids 1999:639-42). Microorganisms suitable for producing n-3 PUFA are found, for example, in bacteria of the genus *Vibrio* (e.g.: *Vibrio marinus*) or among the dinoflagellates (Dinophyta), there particularly the genus *Crypthecodinium*, such as *C. cohnii*, or among the Stramenopiles, such as Pinguiophyceae, e.g. Glossomastix, Phaeomonas, Pinguiochrysis, Pinguiococcus and Polydochrysis. Preferred microorganisms for the fermentative production of PUFA belong to the Stramenopiles (or Labyrinthulomycota), in particular to the order Thraustochytriales, (Thraustchytriidea) and there again, in particular, to the genera *Japonochytrium, Schizochytrium, Thraustochytrium, Althornia, Labyrinthuloides, Aplanochytrium* and *Ulkenia*.

It is known that some of the mentioned microorganisms can be used for industrial production of fatty acids and corresponding processes have been described. Accordingly, the international patent application WO 91/07498 A1 discloses the production of PUFAs using organisms of the genera *Schizochytrium* and *Thraustochytrium*. WO 91/11918 A1 discloses the production of PUFAs using *Crypthecodinium cohnii*, WO 96/33263 A1 and the corresponding European patent application EP 0 823 475 A1 describes the production of PUFAs using microorganisms of the genus *Schizochytrium*, while the patent application WO 98/03671 discloses the production of PUFAs using microorganisms of the genus *Ulkenia*.

The natural habitat of the described microorganisms and in particular of Labyrinthulomycota is a marine habitat. Consequently, these microorganisms are usually cultivated in salt-containing media, where, for the purpose of the present invention, the salt content of sea water is defined as 32-35 g/L and a content of 90-95% of sodium and chloride. Typical media for cultivating marine microorganisms such as *Thraustochytrium* or *Schizochytrium* are based on sea water (e.g. ATCC (American Type Culture Collection) 790 By+medium [yeast extract 1.0 g, peptone 1.0 g, D+glucose 5.0 g, sea water 1 L]). It is, however, also known that microorganisms of the order Thraustochytriales can survive in a culture medium with very low salinity. However, below a limit of 7.5-15 g salt/L, corresponding to a salinity of 7.5-15‰, its growth is described as being only very low and without intermediate maximum levels in the low salinity range. Optimal growth rates are only achieved above the abovementioned salinity limit (Fan et al. Botanica Marina 45, 2002, pp. 50-57).

A frequently occurring problem of fermentative processes is presented by strong pH variations in the course of the cultivation as a result of the appearance of metabolic products and/or the consumption of individual media components. This applies in particular to salt rich media for fermentation of marine microorganisms. For this reason, such fermentations often require pH-regulating means. In the case of large scale fermentations, however, pH control leads to substantial additional costs. Here, additional containers are required for adding acids and bases, which could otherwise be used elsewhere for the infeed of additive components. Moreover, the titration for regulating the pH value must be technically controlled. In connection with the fermentation of Labyrinthulomycota for obtaining PUFA on a production scale, pH value controlled cultivation methods are used in the state of the art.

pH value control through buffer systems otherwise customary in cell culturing has disadvantages, however. Thus, the buffer capacity of, for example, TRIS, HEPES and MOPS is insufficient in the pH range required for PUFA fermentation because of their $pK_a$ values of more than 7. In addition, TRIS is a bad buffer in pH ranges of less than 7.5, a potentially reactive primary amine and can actively take part in a variety of biological reactions. Phosphate buffer, a buffer that is also frequently used, has the characteristic of precipitating out of solution in the presence of divalent cations and is further a bad choice for fermentative processes requiring or consuming phosphate. Acetate buffers are not suitable due to their narrow buffering range and because of the fact that they are metabolized during the course of the fermentation. Moreover, many alternative buffer systems are uneconomic because of high costs.

In the light of the state of the art, it was therefore an object of the present invention to provide a novel, simple and economic cultivating method for marine microorganisms. Considerable simplification of the process control should be achieved hereby. Apart from being cost effective, the method should enable the high yield production of high purity PUFAs.

This and further not explicitly described tasks, which can, however, be derived or deduced without difficulty from the relations discussed in the introduction, are achieved by the object defined in the claims of the present invention.

An advantageous method for cultivating microorganisms of the order Thraustochytriales is provided by the method defined in claim 1. This method comprises cultivating in a medium, the pH value of which is stabilized exclusively by means of $CaCO_3$, comprising a $CaCO_3$ content of 3-15 g/L and, if applicable, the following isolation of the PUFAs from the microorganisms and/or the culture medium.

The invention further comprises a method for producing high purity PUFAs.

Preferred PUFAs are, according to the invention, DHA, DPA and EPA.

Particularly, the microorganisms cultivated by means of the abovementioned method present a production of more than 10%, preferably more than 14%, and very particularly preferably more than 18% DHA per dry biomass.

Particularly, the microorganisms cultivated by means of the abovementioned method present a production of more than 1%, preferably more than 2%, and very particularly preferably more than 3% DPA per dry biomass.

The PUFAs can be obtained in high yield and purity by isolating the PUFAs from the microorganisms (biomass) and/or culture medium following the cultivation.

Furthermore, the present invention comprises a method for producing biomass, where the biomass is provided by the cultivation method according to the invention.

This biomass can be used in all imaginable ways. In particular, this biomass can be used, for example in dried form (dry biomass), directly as foodstuff or animal feed.

In addition, the invention also comprises an oil type, which is obtained by carrying out the cultivation method according to the invention and by isolating said oil from the microorganisms and/or culture medium.

In particular, this is an oil type which, apart from many other preferred applications, can be advantageously used for human nutrition.

Under the conditions according to the invention, the microorganisms thereby show a production of more than 30 wt % oil, preferably of more than 35 wt % oil per unit of weight of dry biomass.

According to the invention, oil is understood to be a proportion of at least 70% neutral lipids and at least 2% phospholipids, which corresponds to the normal fatty acid spectrum of Thraustochytriales known to the person skilled in the art. The neutral lipids thereby consist of at least 80% triglycerides and other compounds such as diacylglycerides, sterols, etc. Furthermore, the triglyceride weight fraction comprises about 95% fatty acids and 5% glycerin.

The possibility of fermenting a marine microorganism for producing PUFA without extreme pH value regulation, in particular under conditions enabling fast growth at high glucose consumption, was totally surprising. It is precisely under such conditions where in the fermentation of marine microorganisms the lack of suitable pH control very quickly leads to medium acidification, which results in a cessation of growth (see example 1 and Wen, Z.-Y. and Chen, F., 2003, Biotechnology Advances 21, 273-294).

The method according to the invention surprisingly gets by without the addition of other pH value stabilizing means. According to the invention, pH value stabilizing means are understood to be both the addition of acid or base from addition tanks regulated in dependence on the pH value established during the culture and the use of buffer systems in the medium itself, although no economically exploitable cultivation methods using buffer systems such as, for example, TRIS or phosphate buffer are known to the inventors.

According to the invention, $CaCO_3$ is the essential means for pH value stabilization. Even so, adding acid or base to the culture to adjust the pH value may be necessary under certain conditions. Such addition is included in the invention, as long as $CaCO_3$ remains the essential means for pH stabilization. If, for example, the pH value drops below a specific target value during cultivation because of an exceptionally fast growth of the microorganisms, then this target value can be temporarily adjusted by adding acid or base, without this addition being the essential means for pH value regulation.

The terms pH value regulation and pH value control or pH value stabilization are used synonymously in the invention.

Essential means remains $CaCO_3$, when the value of the difference in the pH values which can be measured with or without acid addition—with $CaCO_3$ addition according to the invention in each case—is smaller or equal to 1, preferably smaller or equal to 0.75, particularly preferably smaller or equal to 0.5, very particularly preferably smaller or equal to 0.2, and most particularly preferably smaller or equal to 0.1. Such addition of acids and/or bases is understood to be a minor addition of acids and/or bases according to the invention, which is included in the invention.

Preferred are cultivation systems not requiring the use of any acid and/or base addition.

In addition, many alternative buffer systems are uneconomical due to higher costs compared to the use of calcium carbonate.

The high efficacy of calcium carbonate as buffer for cultivating microorganisms of the order Thraustochytriales is surprising, since the carbon dioxide formed only has limited solubility in water, which leads to a decreasing buffer capacity during fermentation.

Surprisingly, not only the fermentation up to the complete glucose consumption was possible, but, in addition to that, the proportion of PUFA in the biomass significantly increased when using the calcium carbonate stabilized medium according to the invention. Even more surprising is that the glucose utilization and, related to that, the PUFA production is accelerated, thereby leading to an increased space-time yield.

Until the present invention, no known fermentation process was available for producing n-3 fatty acids in microorganisms of the order Thraustochytriales using a medium pH-stabilized with calcium carbonate, where it was possible to dispense with further pH value stabilizing means.

PUFAs are polyunsaturated long-chain fatty acids with a chain length >C12 comprising at least two double bonds. PUFAs which can be produced following the method according to the present invention are in particular n-3 fatty acids and n-6 fatty acids.

In the sense of the present invention, n-3 fatty acids (omega-3 fatty acid, ω-3 fatty acids) are understood to be polyunsaturated long-chain fatty acids with a chain length >C12 comprising at least two or more double bonds, where the first double bond is constituted between the carbon atoms C3 and C4 starting from the alkyl end. Accordingly, for n-6 fatty acids the first double bond is located between the carbon atoms C6 and C7 starting from the alkyl end.

Microorganisms belonging to the group of the Labyrinthulomycota are considered for the production of PUFAs following the method according to the present invention. Microorganisms of the order Thraustochytriales (Thraustchytriidea) are preferred (Lewis, T. E., Nichols, P. D., McMeekin, T. A., The Biotechnological Potential of Thraustochytrids, Marine Biotechnology, 1999, S. 580-587 and Porter, D. Phylum Labyrinthulomycota in Handbook of protoctista: the structure, cultivation, habitats, and life histories of the eukaryotic microorganisms and their descendants exclusive of animals, plants, and fungi: a guide to the algae, ciliates, foraminifera, sprorozoa, water molds, and other protoctists. Editors: Margulis, L, Corliss, J. O., Melkonian, M. and Chapman, D. J., editorial coordinator, McKhann, H. I., Jones and Bartlett Publishers, ISBN 0-86720-052-9 1990, S. 388-398). Particularly preferred are microorganisms of the genera *Japonochytrium, Schizochytrium, Thraustochytrium Althornia, Labyrinthuloides, Aplanochytrium* and *Ulkenia*. Of these, *Schizochytrium, Thraustochytrium* and *Ulkenia* are very particularly preferred. Particularly preferred are: *Japonochytrium* sp. ATCC 28207, *Thraustochytrium aureum* (particularly ATCC 28211 and ATCC 34304), *Thraustochytrium roseum* ATCC 28210 *Thraustochytrium* sp. ATCC 20890, ATCC 20891, ATCC 20892 and ATCC 26185, *Schizochytrium aggregatum* ATCC 28209, *Schizochytrium* sp. ATCC 20888 and ATCC 20889, *Schizochytrium SR*21, as well as *Ulkenia* sp. SAM 2179 and SAM 2180.

Microorganisms suitable for the method according to the invention are both wild type forms and mutants and strains derived therefrom as well as recombinant strains of the corresponding organisms. The present invention especially comprises mutants or recombinant strains for increasing the production of PUFA.

The microorganisms according to the present invention are cultivated by inoculating a liquid or a solid medium with a preculture of these organisms.

Culture techniques suitable for microorganisms of the order Thraustochytriales are well known to the person skilled in the art. Typically, but not exclusively, the culture is carried out by means of aqueous fermentation in a corresponding container. Examples for typical containers for such type of fermentation comprise shaking flasks or bioreactors, such as for example STRs (stirred tank reactors) or bubble columns. The culture is typically carried out at temperatures of between 10° C. and 40° C., preferably between 20° C. and 35° C., particularly preferably between 25° C. und 30° C., more particularly preferably between 27° C. und 29° C. and in particular at 28±0.5° C.

In a preferred embodiment of the present invention the calcium carbonate content of the pH-stabilized medium corresponds to a value in the range of 3 g/L to 15 g/L, preferably of 4 g/L to 12 g/L and particularly preferably of 5 g/L to 10 g/L. Very particularly preferred is a calcium carbonate content of 7.5±0.5 g/L.

The pH-stabilized medium further preferably comprises one or more carbon sources, as well as one or more nitrogen sources. Substances usable as carbon and nitrogen sources for cultivating microorganisms of the order Thraustochytriales are well known to the person skilled in the art.

Usable carbon sources are for example carbohydrates such as glucose, fructose, xylose, sucrose, maltose, soluble starch, fucose, glucosamine, dextran, glutamic acid, molasses, glycerin or mannitol or also fats and oils or vegetable hydrolysates.

Usable natural nitrogen sources are, for example, peptone, yeast extract, malt extract, meat extract, casamino acids, corn steep liquor or soy beans, usable organic nitrogen sources are, for example, glutamate and urea, but also inorganic nitrogen sources such as, for example, ammonium acetate, ammonium hydrogen carbonate, ammonium sulfate or ammonium nitrate can be used as nitrogen source.

In addition to calcium carbonate, the pH-stabilized medium can contain all other components known to the person skilled in the art to assist the cultivation of microorganisms of the order Thraustochytriales, in particular inorganic salts of, for example, Ca, Mg, K, Fe, Ni, Co, Cu, Mn, Mo or Zn. Phosphates such as potassium hydrogen phosphate, or chlorides such as magnesium chloride, sulfates such as ammonium sulfate, magnesium sulfate, iron sulfate or sodium sulfate may be mentioned as examples. Further usable inorganic salts are, for example, halogenides, such as potassium bromide or potassium iodide and also other carbonates such as sodium hydrogen carbonate.

Where applicable, the medium can comprise additional macro- or micronutrients, such as amino acids, purine, pyrimidine, corn steep liquor, protein hydrolysates, vitamins (water soluble and/or water insoluble) and other media components well known to the person skilled in the art. Antifoaming agents can be added, if necessary. The medium can contain complex components or be chemically defined.

The amounts of the individual components can vary, as long as there is no negative effect on the growth or productivity of the microorganisms. The person skilled in the art can easily determine the composition for each individual case according to the requirements of the microorganism. Generally, the carbon source is added at a concentration of up to 300 g/L and the nitrogen source at a concentration of 1 to 30 g/L. Preferably, the nitrogen content is adjusted in dependence of the carbon content of the medium.

A particularly preferred pH value stabilized medium comprises glucose, yeast extract, corn steep liquor (CSL), magnesium chloride, calcium carbonate, calcium chloride, sodium sulfate and potassium phosphate.

The pH value of the medium is set prior to the start of the fermentation to a range of 3 to 10, preferably 4 to 8, particularly preferably 5 to 7 and very particularly preferably to about 6 by adding a corresponding acid or base.

The medium is subsequently sterilized. Techniques for sterilizing media are well known to the person skilled in the art, autoclaving and sterile filtration may be mentioned as examples.

Cultivation can take place batchwise, in a fed-batch mode or continuously, as it is generally known to the person skilled in the art.

Batch or fed-batch cultivation usually takes place over a period of 1 to 12 days, preferably 2-10 days, particularly preferably 3-9 days.

The media components can be added to the medium individually or as a mixture, a previously prepared mixture being also possible. The components, in particular the carbon and nitrogen source(s) or specific medium additions can be added prior to or during the cultivation. The addition can be repeated once or several times or can also take place continuously.

The produced PUFA are generally available in form of neutral fats, for example as triacylglycerides, or polar lipids such as, for example, phosphatidylcholine, phosphatidylethanolamine or phosphatidylinositol.

For the purpose of the present invention, the terms PUFA, n-3 fatty acid or n-3 active substances are understood to be all possible forms in which the corresponding fatty acids can exist, i.e. as free fatty acids, esters, triglycerides, phospholipids or other derivatives. All these substances are summarized in the following text and the terms are used synonymously. Furthermore, the PUFAs can be converted and concentrated by means of chemical or biocatalytic transesterification, for example with the help of suitable enzymes (lipases), before or after isolation from the culture.

The isolation of PUFAs from the fermented microorganisms or medium and the analysis of the fatty acid spectrum is carried out using common procedures known to the person skilled in the art (Wanasundara, U. N., Wanasundara, J., Shahidi, F., Omega-3 fatty acid concentrates: a review of production technologies, Seafoods—Quality, Technology and Nutraceutical Applications, 2002, S. 157-174).

The pH-stabilized fermentation medium forming the basis for the method according to the invention is described hereinafter by way of some examples. The fermentation medium as well as the invention is, however, not limited to these examples.

EXAMPLE 1

Fermentation of *Ulkenia* sp. SAM 2179 Strain for the Production of PUFA in Different Culture Media pH-stabilized Exclusively by Different Quantities of $CaCO_3$

*Ulkenia* sp. SAM 2179 strain was cultivated in 50 mL medium in 300 mL Erlenmeyer flasks with a baffle.
Media Composition:

| Fermentation medium: | Glucose | 150 g/L |
|---|---|---|
| | Corn steep liquor | 3.75 g/L |
| | $KH_2PO_4$ | 3 g/L |
| | $Na_2SO_4$ | 1 g/L |
| | $MgCl_2 \cdot 6H_2O$ | 1 g/L |
| | $CaCl_2 \cdot 2H_2O$ | 0.3 g/L |
| | $(NH_4)_2SO_4$ | 5 g/L |
| $CaCO_3$ addition per 50 mL flask: | Medium 1.1 | 0 g/L |
| | Medium 1.2 | 1 g/L |
| | Medium 1.3 | 2 g/L |
| | Medium 1.4 | 5 g/L |
| | Medium 1.5 | 10 g/L |
| Set pH value to 6.0 with NaOH and autoclave | | |
| Culture conditions: | | |
| Temperature (° C.): | 28 | |
| Shaking rate (rpm): | 150 | |

Cell harvest was carried out by centrifugation after 96 h of cultivation. The cells were subsequently freeze dried and the dry biomass determined. Cell digestion and fatty acid determination was carried out by means of 2 hour long heat treatment in 10% methanolic hydrochloric acid at 60° C. (under stirring). The esters were analyzed in a gas chromatograph to determine the fatty acid composition.

greater quantities of $CaCO_3$ buffer lead to a stabilization of the pH value during the culture (medium 1.4 and 1.5). Here, an increasing $CaCO_3$ concentration also leads to an increased glucose consumption during the culture. Because of the pH value stabilization and the increased glucose consumption associated therewith, higher biomass values are achieved and, as a result of that, also higher DHA space-time yields of about 2 g/L×d under the abovementioned conditions.

EXAMPLE 2

Fermentation of *Ulkenia* sp. SAM 2179 Strain for the Production of PUFA in Different Culture Media, pH-value Stabilized Exclusively by Different Quantities of $CaCO_3$, up to Glucose Limitation

*Ulkenia* sp. SAM 2179 strain was cultivated in 50 mL medium in 300 mL Erlenmeyer flasks with a baffle up to complete glucose consumption.
Media Composition:

| Fermentation medium: | Glucose | 150 g/L |
|---|---|---|
| | Corn steep liquor | 3.75 g/L |
| | $KH_2PO_4$ | 3 g/L |
| | $Na_2SO_4$ | 1 g/L |
| | $MgCl_2 \cdot 6H_2O$ | 1 g/L |
| | $CaCl_2 \cdot 2H_2O$ | 0.3 g/L |
| | $(NH_4)_2SO_4$ | 5 g/L |
| $CaCO_3$ addition per 50 mL flask: | Medium 1.4 | 5 g/L |
| | Medium 1.5 | 10 g/L |
| Set pH value to 6.0 with NaOH and autoclave | | |
| Culture conditions: | | |
| Temperature (° C.): | 28 | |
| Shaking rate (rpm): | 150 | |

Cell harvest was carried out by centrifugation after 144.5 h of cultivation. The cells were subsequently freeze dried and

TABLE 1

Fermentation parameter in dependence on the calcium carbonate concentration

| | $CaCO_3$ (g/L) | Glucose consumption (g/L) | pH value | DBM (g/L) | DHA area (%) | DHA/DBM (%) | DHA (g/L) | DHA-STY (g/L × d) |
|---|---|---|---|---|---|---|---|---|
| Medium 1.1 | 0 | 43.0 | 1.85 | 22.72 | 48.3 | 3.35 | 0.76 | 0.19 |
| Medium 1.2 | 1 | 59.0 | 2.31 | 30.32 | 44.0 | 4.91 | 1.49 | 0.37 |
| Medium 1.3 | 2 | 81.7 | 2.84 | 38.58 | 43.9 | 9.90 | 3.82 | 0.96 |
| Medium 1.4 | 5 | 108.4 | 5.02 | 52.99 | 44.8 | 15.72 | 8.33 | 2.08 |
| Medium 1.5 | 10 | 111.9 | 4.78 | 52.32 | 45.5 | 13.23 | 6.92 | 1.73 |

DBM: Dry biomass;

DHA/DBM: wt % DHA (docosahexaenoic acid) per unit of weight DBM;

g/L × d space-time yield in grams per liter per day;

STY: space-time yield;

DHA area (%) Proportion of DHA in the fatty acid spectrum

The fermentation of *Ulkenia* sp. SAM 2179 in a fermentation medium lacking sufficient pH stabilization leads to a slowdown in the glucose consumption during the course of the fermentation and to a cessation of growth as a result of a sharp drop in the pH value (see medium 1.1.-1.3.). Only the dry biomass determined. Cell digestion and fatty acid determination was carried out by means of 2 hour long heat treatment in 10% methanolic hydrochloric acid at 60° C. (under stirring). The esters were analyzed in a gas chromatograph to determine the fatty acid composition.

TABLE 2

Fermentation parameter after glucose limitation

| | CaCO$_3$ (g/L) | Glucose consumption (g/L) | pH value | DBM (g/L) | DHA area (%) | DHA/DBM (%) | DHA (g/L) | DHA-STY (g/L × d) |
|---|---|---|---|---|---|---|---|---|
| Medium 1.4 | 5 | 150.0 | 6.49 | 58.52 | 47.7 | 22.20 | 12.99 | 2.14 |
| Medium 1.5 | 10 | 150.0 | 6.58 | 64.65 | 46.7 | 20.54 | 13.28 | 2.19 |

The fermentation of *Ulkenia* sp. SAM 2179 in a medium buffered with 5 g/L resp. 10 g/L CaCO$_3$, respectively, enables cultivation up to glucose limitation without a strong drop in the pH value. The thereby achievable biomass and the proportion of DHA per biomass are, with about 58-64 g/L biomass and 20-22% DHA/DBM, corresponding to complete glucose consumption, very high. It is found that a higher CaCO$_3$ concentration (10 g/L) leads to a larger amount of biomass, although the proportion of essential PUFA DHA per biomass is slightly reduced in relation to the lower CaCO$_3$ (5 g/L). However, the DHA space-time yield obtained therewith remains approximately the same for both concentrations.

EXAMPLE 3

Cultivation of *Ulkenia* sp. SAM 2179 Strain for the Production of PUFA under Optimized Fermentation Conditions

*Ulkenia* sp. SAM 2179 strain was cultivated in 50 mL medium in 300 mL Erlenmeyer flasks with a baffle up to complete glucose consumption. Optimization of the fermentation resulted from a CaCO$_3$ concentration of 7.5 g/L and a modified preculture. For the preculture, instead of using a stand culture in DH1 medium, a shake culture was used with the same medium (48 h, 150 rpm and 28° C.).
Media Composition:

| Preculture medium: | DH1 medium | |
|---|---|---|
| Glucose monohydrate (g/L): | 56.25 | |
| Yeast extract (g/L): | 12.5 [Difco] | |
| Tropic Marin (g/L): | 16.65 [Dr. Biener GmbH, Wartenberg, Germany] | |
| pH value set to 6.0 with HCl | | |
| Fermentation medium: | Glucose | 150 g/L |
| | Corn steep liquor | 3.75 g/L |
| | KH$_2$PO$_4$ | 3 g/L |
| | Na$_2$SO$_4$ | 1 g/L |
| | MgCl$_2$x6H$_2$O | 1 g/L |
| | CaCl$_2$x2H$_2$O | 0.3 g/L |
| | (NH$_4$)$_2$SO$_4$ | 5 g/L |
| CaCO$_3$ addition per 50 mL flask: | Medium 1.6 | 7.5 g/L |
| Set pH value to 6.0 with NaOH and autoclave | | |
| Culture conditions: | | |
| Temperature (° C.): | 28 | |
| Shaking rate (rpm): | 150 | |

The cell harvest was carried out by centrifugation after 99.75 h of cultivation. The cells were subsequently freeze dried and the dry biomass determined. Cell digestion and fatty acid determination was carried out by means of 2 hour long heat treatment in 10% methanolic hydrochloric acid at 60° C. (under stirring). The esters were analyzed in a gas chromatograph to determine the fatty acid composition.

TABLE 3

Fermentation parameters under optimized buffer conditions

| | CaCO$_3$ (g/L) | Glucose consumption (g/L) | pH value | DBM (g/L) | DHA area (%) | DHA/DBM (%) | DHA (g/L) | DHA-STY (g/L × d) |
|---|---|---|---|---|---|---|---|---|
| Medium 1.6 | 7.5 | 150.0 | 6.76 | 63.84 | 44.1 | 23.06 | 14.72 | 3.54 |

Using optimized fermentation conditions, under which *Ulkenia* sp. SAM 2179 was first cultivated for 48 h at 28° C. and 150 rpm in DH1 medium, the DHA space-time yield could be substantially improved to more than 3.5 g/L×d. This results primarily from a faster growth, whereby the glucose limitation was reached in less than 100 h. The use of 7.5 g/L CaCO$_3$ in the fermentation medium enables a pH stabilization required for optimized cultivation. The use of 7.5 g/L CaCO$_3$ resulted from the results of example 2, in which 10 g/L CaCO$_3$ resulted in higher biomass values, while 5 g/L CaCO$_3$ gave rise to better DHA values. An optimal CaCO$_3$ concentration for DHA production (i.e. largest possible amount of biomass with highest possible DHA content) was consequently suspected between 5 and 10 g/L CaCO$_3$. In addition to the stabilization of the pH value, the use of the fermentation medium according to the invention results in a surprisingly high DHA space-time yield of more than 3 g/L×d at the time of glucose limitation. Similar biomass values to those in example 2 were obtained in this case, the proportion of DHA per dry biomass and the DHA quantities achieved were, however, larger (more than 10%).

EXAMPLE 4

Fermentation of *Ulkenia* sp. SAM 2179 Strain for the Production of PUFA in Culture Medium with and without pH Stabilization by CaCO$_3$

*Ulkenia* sp. SAM 2179 strain was cultivated in a 5L fermenter up to complete glucose consumption.
Media Composition:

| Fermentation medium: | Glucose | 150 g/L |
|---|---|---|
| | Corn steep liquor | 3.75 g/L |
| | KH$_2$PO$_4$ | 3 g/L |
| | Na$_2$SO$_4$ | 1 g/L |
| | MgCl$_2$x6H$_2$O | 1 g/L |

-continued

|  |  |  |
|---|---|---|
|  | $CaCl_2 \cdot x2H_2O$ | 0.3 g/L |
|  | $(NH_4)_2SO_4$ | 5 g/L |
| For fermentation with pH control: | Set pH value to 4.0 with $H_3PO_4$ and autoclave | |
| For fermentation without pH control: | Set pH value to 6.0 with NaOH and autoclave as well as addition of 7.5 g/L $CaCO_3$ | |
| Culture conditions: | | |
| Temperature (° C.): | 28 | |
| Ventilation: | 0.8 vvm | |

Fermentation with and without pH Control

TABLE 4

Fermentation parameters with and without pH control

| pH control | $CaCO_3$ (g/L) | Glucose consumption (g/L) | Time for glucose consumption (h) | DBM (g/L) | DHA area (%) | DHA/DBM (%) | DHA (g/L) | DHA-STY (g/L × d) |
|---|---|---|---|---|---|---|---|---|
| + | 0 | 150.0 | 162 | 66.9 | 47.2 | 25.9 | 17.35 | 2.5 |
| − | 7.5 | 150.0 | 150 | 67.8 | 46.7 | 26.9 | 18.30 | 2.9 |

The use of the $CaCO_3$-stabilized fermentation medium according to the invention enables cultivation of *Ulkenia* sp. SAM 2179 up to glucose limitation without pH control also in a 5L fermentation scale. The use of sufficient quantities of $CaCO_3$ leads to a faster growth as a result of the accelerated glucose consumption. In addition, larger biomasses are achieved. Furthermore, in connection to this, a greater proportion of DHA per biomass and larger quantities of DHA are achieved during fermentation. This leads to a not insignificant increase in the DHA space-time yield of more than 15% for $CaCO_3$-buffered fermentation compared to pH-controlled fermentation.

EXAMPLE 5
Fermentation of *Schizochytrium* sp. SR21 for the Production of PUFA in Fermentation Medium 1.6 Stabilized by 7.5 g/L $CaCO_3$

*Schizochytrium* sp. SR 21 strain was cultivated in 50 mL medium in 300 mL Erlenmeyer flasks with a baffle up to complete glucose consumption.

Media Composition:

| Preculture medium: | GY medium | |
|---|---|---|
| Glucose (g/L): | 30.0 | |
| Yeast extract (g/L): | 10.0 [Difco] | |
| Tropic Marin (g/L): | 16.65 [Dr. Biener GmbH, Wartenberg, Germany] | |
| pH value set to 6.0 with HCl | | |
| Fermentation medium: | Glucose | 150 g/L |
|  | Corn steep liquor | 3.75 g/L |
|  | $KH_2PO_4$ | 3 g/L |
|  | $Na_2SO_4$ | 1 g/L |
|  | $MgCl_2 \cdot x6H_2O$ | 1 g/L |
|  | $CaCl_2 \cdot x2H_2O$ | 0.3 g/L |
|  | $(NH_4)_2SO_4$ | 5 g/L |
| $CaCO_3$ addition per 50 mL flask: | Medium 1.6 | 7.5 g/L |
| Set pH value to 6.0 with NaOH and autoclave | | |
| Culture conditions: | | |
| Temperature (° C.): | 28 | |
| Shaking rate (rpm): | 150 | |

The cell harvest was carried out by centrifugation after 96 h of cultivation. The cells were subsequently freeze dried and the dry biomass determined. Cell digestion and fatty acid determination was carried out by means of 2 hour long heat treatment in 10% methanolic hydrochloric acid at 60° C. (under stirring). The esters were analyzed in a gas chromatograph to determine the fatty acid composition.

TABLE 5

Fermentation parameters under optimized buffer conditions

|  | $CaCO_3$ (g/L) | glucose consumption (g/L) | pH value | DBM (g/L) | DHA area (%) | DHA/DBM (%) | DHA (g/L) | DHA-STY (g/L × d) |
|---|---|---|---|---|---|---|---|---|
| SR 21 | 7.5 | 150.0 | 7.35 | 66.12 | 34.4 | 15.28 | 10.10 | 2.52 |

The medium being pH-stabilized using $CaCO_3$ described in the invention also leads to an optimization of the production of PUFA in the case of other organisms belonging to Labyrinthulomycota. It is thus possible to ferment the microorganism *Schizochytrium* sp. SR21 strain in the medium forming the object of the invention. The space-time yield of the essential PUFA, DHA in SR 21 is slightly lower than in *Ulkenia* sp. SAM 2179 (see example 3), but it is more than 15% (w/w) of the total dry biomass in relation to n-3 PUFA DHA. This example shows that the optimized pH-stabilized medium forming the object of the present invention enables fermentation without pH control for the production of PUFAs also in further members of Labyrinthulomycota.

The invention claimed is:

1. A method for cultivating microorganisms of the order Thraustochytriales comprising the steps of:
   cultivating microorganisms selected from the group comprising *Ulkenia* sp. SAM 2179 or *Schizochytrium* sp. SR 21 in a fermentation medium containing $CaCO_3$ as an essential means for pH value stabilization, where content of $CaCO_3$, in said fermentation medium is 7.5 g/l±0.5 g/l;

wherein the pH value of the fermentation medium is set prior to the start of the fermentation in the range of 5 to 7 by adding a corresponding acid or base;

isolating PUFAs from said microorganisms and/or said fermentation medium wherein the microorganisms bring forth a production of more than 10 wt % docosahexaenoic acid (DHA) per unit of weight of dry biomass.

2. The method according to claim 1, wherein the microorganisms bring forth a production of more than 25 wt % oil per unit of weight of dry biomass.

3. The method according to claim 1, wherein the microorganisms bring forth a production of more than 1% docosapentaenoic acid (DPA) per dry biomass.

4. The method according to claim 1, characterized in that the medium comprises glucose, corn steep liquor, magnesium chloride, calcium chloride, calcium carbonate, sodium sulfate, ammonium sulfate and potassium hydrogen phosphate.

5. The method according to claim 1, characterized in that the cultivation takes place between 10° C. and 40° C.

6. The method according to claim 1, characterized in that the cultivation takes place for 1 to 10 days.

* * * * *